US006211162B1

(12) United States Patent
Dale et al.

(10) Patent No.: US 6,211,162 B1
(45) Date of Patent: Apr. 3, 2001

(54) PULMONARY DELIVERY OF PROTONATED/ACIDIFIED NUCLEIC ACIDS

(75) Inventors: Roderic M. K. Dale, Wilsonville; Steven L. Gatton, Lake Oswego, both of OR (US); Amy Arrow, Bethel, ME (US)

(73) Assignee: Oligos Etc. Inc., Wilsonville, OR (US)

( * ) Notice: Subject to any disclaimer, the term of this patent is extended or adjusted under 35 U.S.C. 154(b) by 0 days.

(21) Appl. No.: 09/282,824

(22) Filed: Mar. 31, 1999

Related U.S. Application Data

(63) Continuation-in-part of application No. 09/222,009, filed on Dec. 30, 1998.
(51) Int. Cl.$^7$ .......................... A61K 51/00; A01N 43/04; C12Q 1/68; C07H 21/02
(52) U.S. Cl. ................ 514/44; 424/1.13; 435/6; 536/23.1; 536/25.1; 536/25.2
(58) Field of Search ................ 536/23.5, 23.1; 435/6; 514/44; 424/1.13

(56) References Cited

U.S. PATENT DOCUMENTS

| 5,294,533 | 3/1994 | Lupski ....................... 435/6 |
| 5,739,309 | * 4/1998 | Dattagupta et al. ................ 536/24.5 |

FOREIGN PATENT DOCUMENTS

| WO 96/29399 | 9/1996 | (WO) . |
| WO 98/03533 | * 1/1998 | (WO) . |

OTHER PUBLICATIONS

Heidenreich et al., Molecular Medicine Today, vol. 1, p. 128–133, 1995.*

Mastrangelo et al., Seminars in Oncology, vol. 23 (1), p. 4–21, Feb. 1996.*

Verma et al., Nature, vol. 389, p. 239–242, Sep. 1997.*

Eck et al., Goodman & Gilman's The Pharmacological Basis of Therapeutics, Ninth Editiion, McGraw–Hill, New York, p. 77–101, 1996.*

Burns et al., *Advances in Pediatric Infectious Diseases* 8:53–67 (1993).

Gould et al., *Lancet*, 22:1377–79 (1981).

Levy et al., *J. Infect. Dis.*, 148:1069–1076 (1983).

Pennington, *Rev. Infect. Dis.*, 3:67–73 (1981).

Archer et al., 1994, *Antimicrob. Agents Chemother.* 38:2231–2237.

Bennett, 1993, *Antisense Res. Devel.* 3:235–241.

Cohen, 1989, *Oligodeoxynucleotides; Antisense Inhibitors of Gene Expression*, Boca Raton, FL, CRC Press.

Crooke, 1997, in *Antisense Nucleic Acid and Antisense RNA: Novel Pharmacological and Therapeutic Agents*, B. Weiss ed., CRC Press Boca Raton, FL., p. 17.

Goth, 1974, *Medical Pharmacology: Principles and Concepts*, The C.V. Mosby Company, Saint Louis, MO.

Hoke et al., 1991, *Nucl. Acids Res.* 19:5743.

Hughes et al., 1995, *Pharmaceutical Research* 12:817.

Krieg et al., 1995, *Nature* 374:546–549.

Kristinsson, 1995, *Microb. Drug Resistance* 1(2):121.

Woodford et al., 1995, *J. Antimicrob. Chemother.* 35:179–184.

Yamamoto et al., 1994, *Antisense Res. Devel.* 4:119–122.

Zabransky et al., 1995, *J. Clin. Microbiol.* 33(4):791–793.

* cited by examiner

Primary Examiner—Deborah J. R. Clark
Assistant Examiner—Shin-Lin Chen
(74) Attorney, Agent, or Firm—Bozicevic, Field & Francis LLP; Dianna L. DeVore

(57) ABSTRACT

The present invention provides a method of treating bacterial respiratory infections by pulmonary administration of protonated/acidified nucleic acids. These modified nucleic acids are effective as bactericidal and/or bacteriostatic agents without regard to the class of bacteria, so are especially useful when diagnosis is difficult or when multiple infectious organisms are present. The antibiotic activity of nucleic acids of the invention is not dependent on either the specific sequence of the nucleic acid or the length of the nucleic acid molecule.

15 Claims, No Drawings

SEQUENCE LISTING

```
<160> NUMBER OF SEQ ID NOS:  9

<210> SEQ ID NO 1
<211> LENGTH: 9
<212> TYPE: DNA
<213> ORGANISM: Artificial Sequence
<220> FEATURE:
<223> OTHER INFORMATION: synthesized modified oligonucleotide

<400> SEQUENCE: 1
```

```
cgccattgg                                                              9

<210> SEQ ID NO 2
<211> LENGTH: 6
<212> TYPE: DNA
<213> ORGANISM: Artificial Sequence
<220> FEATURE:
<223> OTHER INFORMATION: synthesized modified oligonucleotide

<400> SEQUENCE: 2 cgccat                                                                 6

<210> SEQ ID NO 3
<211> LENGTH: 12
<212> TYPE: DNA
<213> ORGANISM: Artificial Sequence
<220> FEATURE:
<223> OTHER INFORMATION: synthesized modified oligonucleotide

<400> SEQUENCE: 3
acgcgccatt gg                                                         12

<210> SEQ ID NO 4
<211> LENGTH: 21
<212> TYPE: DNA
<213> ORGANISM: Artificial Sequence
<220> FEATURE:
<223> OTHER INFORMATION: synthesized modified oligonucleotide

<400> SEQUENCE: 4
ggaacgcgcc attggtatat c                                               21

<210> SEQ ID NO 5
<211> LENGTH: 12
<212> TYPE: DNA
<213> ORGANISM: Artificial Sequence
<220> FEATURE:
<223> OTHER INFORMATION: synthesized modified oligonucleotide

<400> SEQUENCE: 5
aaaaaaaaaa aa                                                         12

<210> SEQ ID NO 6
<211> LENGTH: 12
<212> TYPE: RNA
<213> ORGANISM: Artificial Sequence
<220> FEATURE:
<223> OTHER INFORMATION: synthesized modified oligonucleotide

<400> SEQUENCE: 6
uuuuuuuuuu uu                                                         12

<210> SEQ ID NO 7
<211> LENGTH: 12
<212> TYPE: DNA
<213> ORGANISM: Artificial Sequence
<220> FEATURE:
<223> OTHER INFORMATION: synthesized modified oligonucleotide

<400> SEQUENCE: 7
gggggggggg gg                                                         12

<210> SEQ ID NO 8
<211> LENGTH: 12
<212> TYPE: DNA
```

-continued

```
<213> ORGANISM: Artificial Sequence
<220> FEATURE:
<223> OTHER INFORMATION: synthesized modified oligonucleotide

<400> SEQUENCE: 8
cccccccccc cc                                                 12

<210> SEQ ID NO 9
<211> LENGTH: 12
<212> TYPE: DNA
<213> ORGANISM: Artificial Sequence
<220> FEATURE:
<223> OTHER INFORMATION: synthesized modified oligonucleotide

<400> SEQUENCE: 9
acgcgccatt at                                                 12
```

US 6,211,162 B1

PULMONARY DELIVERY OF PROTONATED/ACIDIFIED NUCLEIC ACIDS

This application is a continuation-in-part of our earlier filed application Ser. No.: 09/222,009, filed Dec. 30, 1998, to which we claim priority under 35 U.S.C. §120 and which is incorporated herein by reference in its entirety.

FIELD OF THE INVENTION

The invention relates to pulmonary delivery of antibiotics, and in particular delivery of antibiotics to alleviate respiratory infections.

BACKGROUND OF THE INVENTION

Bacterial respiratory infections are a major health problem in the United States, and especially amongst patients with compromised immunological defense mechanisms. Patients with Cystic Fibrosis (CF), Acquired Immune Deficiency Syndrome (AIDS), congestive heart failure, chronic lung disease, cancer, and the elderly population all possess an increased risk of respiratory infection. For example, the debilitation of the lungs in CF patients is associated with accumulation of purulent sputum produced as a result of chronic endobronchial infections caused by opportunistic infectious organisms. Nearly all individuals suffering from CF eventually die of respiratory failure.

*P. aeruginosa* is a small, aerobic gram-negative rod that inhabits soil, water, plants, and animals, including humans. Although *P. aeruginosa* occasionally colonizes the skin, external ear, upper respiratory tract or large bowel of healthy humans, these infections are usually mild. Infection by *P. aeruginosa* can be much more serious in immunocompromised individuals, causing a number of complications including: chronic infections of the lower respiratory tract of CF patients; bacteremic pneumonia, which complicates hematopoetic malignancies following chemotherapy-induced severe neutropenia; and primary pneumonia in patients with AIDS, congestive heart failure, and chronic lung disease.

*S. aureus* is a staphylococcal bacteria that is a major health problem due to its tenacity, potential destructiveness, and increasing resistance to antimicrobial agents. Pneumonia arising from *S. aureus* infection most commonly follows tracheal intubation during hospitalization or is secondary to a viral respiratory infection. Such infections are very common in patients who are elderly and/or institutionalized. In addition, respiratory infection of *S. aureus* may cause septic pulmonary embolization in settings such as right-sided endocarditis, which is common in intravenous drug users, and septic thrombophlebitis, which is oftentimes a complication of an indwelling venous catheter. *S. aureus* is also a health problem in immunocompromised patients, as it is often difficult to treat with conventional systemic antibiotics.

Current treatments for these and other pulmonary bacterial infections are often expensive, non-specific, and must use very large doses in order to be effective. In one example, the present treatment of choice for chronic bronchitis or bronchiectasis seen in CF patients is parenteral administration of an aminoglycoside and a beta-lactam active against *P. aeruginosa*. However, aminoglycoside penetration into the bronchial secretions is poor at approximately only about 12% of the peak serum concentration (*Rev. Infect. Dis.*, 3:67 (1981)). According to *Advances in Pediafric Infectious Diseases*, 8:53 (1993), sputum itself is inhibitory to the bioactivity of aminoglycosides because of its high ionic strength and the presence of divalent cations. This inhibitory activity can be overcome by increasing the concentration of aminoglycosides in the sputum to ten times the minimum inhibitory concentration of the particular *P. aeruginosa* isolate (*J Infect. Dis.*, 148:1069 (1983)), but this increases the risk of systemic toxicity including ototoxicity and nephrotoxicity. Intravenous therapy may increase hardship on the patient, and frequently requires hospitalization, which increases treatment costs and exposes the patient to other potential infections.

One of the first studies using aerosolized antibiotics for the treatment of CF was reported in *Lancet*, 22:1377–9 (1981). A controlled, double-blind study on twenty CF patients demonstrated that aerosol administration of carbenicillin and gentamicin can improve the health of CF patients. Unfortunately, the physical properties of many antibiotics, such as aminoglycosides require a relatively high dose of the drug for aerosolization and such treatment then becomes rather expensive.

There is a need in the art for a cost-effective and therapeutically efficacious treatment for bacterial respiratory infections, and especially for respiratory infections in immuno-compromised patients. There is also a need for an efficient method for specifically introducing antibiotic agents to the respiratory tract to the site of the infection.

SUMMARY OF THE INVENTION

The present invention provides a method of treating bacterial respiratory infections by pulmonary administration of protonated/acidified nucleic acids. These modified nucleic acids are effective as bactericidal and/or bacteriostatic agents without regard to the class of bacteria, so are especially useful when diagnosis is difficult or when multiple infectious organisms are present. The antibiotic activity of nucleic acids of the invention is not dependent on either the specific sequence of the nucleic acid or the length of the nucleic acid molecule. The nucleic acids of the invention are protonated/acidified to give a pH when dissolved in water of less than pH 7 to about 1, more preferably less than pH 4.5 to about 1, and even more preferably less than pH 2 to about 1. Formulations of aerosolized protonated/acidified nucleic acids are preferably aerosolized and administered via hand-held, self-contained, disposable units.

The nucleic acids of the invention may have nuclease resistant backbones, acid resistant backbones, and, in their preferred embodiment, have both acid resistant and nuclease resistant backbones.

The preferred method of treatment comprises aerosolized delivery of protonated/acidified nucleic acids to the bronchial tubes of an animal, and in particular humans, in an amount sufficient to inhibit or prevent bacterial growth, to alleviate the symptom of the bacterial growth, or in an amount effective for treatment of a bacterial infection.

In another embodiment, the invention provides for pulmonary delivery of protonated/acidified nucleic acids to treat or prevent a primary respiratory disease involving viral infection, inflammatory diseases, cancer, fungal infections, etc., wherein the nucleic acids targeted to treat these disorders are additionally protonated in order to simultaneously treat or prevent a bacterial infection. Preferably, nucleic acids of this embodiment control expression of a gene known to be involved in the primary respiratory disease, e.g., a gene encoding a viral structural protein or an endogenous gene involved in cancer, e.g., an oncogene.

The dose of nucleic acid administered varies with a number of factors, including the inspiratory rate of the patient, the location of the infected region (i.e., upper or lower respiratory tract), the extent of the infection, and the particular species of bacteria involved in the infection. It is often preferable to target the dosage to a particular area of the lungs to better treat an infected region. For example, to achieve deposition of particles in the lower respiratory tract, e.g., to treat pneumonia, it is desirable to get the aerosolized formulation deeply into the lung. Delivery of particles can be controlled, in part, by adjusting particle sizes. In addition to adjusting particle size, delivery of the protonated/acidified nucleic acids can be obtained by releasing an aerosolized dose at a desired point in a patient's respiratory cycle.

Another object is to provide a method of administering a protonated/acidified oligonucleotide formulation to a patient wherein the formulation is repeatedly delivered to a patient at the same measured inspiratory flow rate (in the range of 0.1 to 2.0 liters/second) and separately determined inspiratory volume (in the range of 0.15 to 1.5 liters). Preferably, the oligonucleotide is from 2 to 100 nucleic acids in length.

Another object is to provide a method of administering a protonated/acidified nucleic acid monomer formulation to a patient wherein the formulation is repeatedly delivered to a patient at the same measured inspiratory flow rate (in the range of 0.1 to 2.0 liters/second) and separately determined inspiratory volume (in the range of 0.15 to 1.5 liters).

It is an object of the invention to use protonated/acidified nucleic acids to treat respiratory ailments caused by pathogenic bacteria.

It is another object of the invention to use protonated/acidified nucleic acids to treat respiratory ailments caused by non-bacterial pathogens, e.g., viral infections and fungal infections, and to simultaneously treat and/or prevent a secondary bacterial infection.

It is yet another object of the invention to treat pulmonary immune response activity by administering protonated/acidified nucleic acids to suppress an immune response and to simultaneously treat and/or prevent a secondary bacterial infection.

It is yet another object of the invention to treat a pulmonary neoplasm by administering protonated/acidified nucleic acids to suppress oncogenesis, metastasis, and/or dedifferentiation and to simultaneously treat and/or prevent a secondary bacterial infection.

It is an advantage of the invention that the mechanism of action of the protonated/acidified nucleic acids appears to be relatively non-specific, allowing them to be effective against any bacterium including clinically relevant pathogenic bacteria.

It is another advantage of the invention that the protonated/acidified nucleic acids are non-toxic to a subject treated with the modified nucleic acids.

It is yet another advantage of the invention that a subject treated with the modified nucleic acids display virtually no unwanted side effects from the nucleic acids.

It is a further advantage that the antibacterial effectiveness of protonated/acidified nucleic acids is neither length- nor sequence-dependent.

These and other objects, advantages, and features of the invention will become apparent to those skilled in the art upon reading the details of the nucleic acids and uses thereof as more fully described below.

DETAILED DESCRIPTION OF PREFERRED EMBODIMENTS

Before the present methods of pulmonary delivery are described, it is to be understood that this invention is not limited to particular methods described, and as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "formulation" is used to describe any single liquid, mixture, solution, suspension or the like which is a flowable liquid at room temperature and comprises a pharmaceutically active amount of the protonated/acidified nucleic acids of the present invention. The formulation is preferably further comprised of a carrier and more preferably is a liquid that has physical properties (e.g., viscosity) such that when the formulation is aerosolized into particles (0.1 to 10 microns in diameter) and inhaled into the lungs of a patient it preferably will reach the targeted portion of the lungs. The carrier may be any pharmaceutically acceptable material and is preferably a flowable liquid which is compatible with the active agent. Formulations are preferably solutions, e.g., aqueous solutions, ethanolic solutions, aqueous/ethanolic solutions, saline solutions, colloidal suspensions and microcrystalline suspensions. The term "formulation" can further include dry powders of protonated/acidified nucleic acids, and preferably oligonucleotides or monomers.

The term "carrier" shall mean a substantially inactive (biologically) component of a formulation such as a pharmaceutically acceptable excipient material which the protonated/acidified nucleic acids are mixed with, suspended or dissolved in. The carrier is preferably a flowable liquid. Useful carriers do not adversely interact with the nucleic acid and have properties that allow for the formation of aerosolized particles, preferably particles having a diameter in the range of 0.1 to 10.0 $\mu$m (more preferably 1 to 5 $\mu$m) when a formulation comprising the carrier and active ingredient is aerosolized. Carriers include water, ethanol, saline solutions and mixtures thereof with pure water being preferred. Other carriers can be used provided that they can be formulated to create a suitable aerosol and do not adversely affect the active component or human lung tissue or nasal passage.

The term "aerosol" means particles of a formulation wherein the particles have a diameter in the range of 0.1 to 10 microns, preferably 1 to 5 $\mu$m, and preferably the total volume of formulation is from 5 $\mu$l to 10,000 $\mu$l. About 10 $\mu$l of particles having a diameter of about 1 to 3 microns are present in a volume of about 50 ml to 2 liters, preferably 100 ml to 1,000 ml.

The terms "air", "particle free air", "aerosol free air," and the like, are used interchangeably herein to describe a volume of air that is substantially free of other material and, in particular, free of particles intentionally added such as particles of formulation which create the aerosol. The term means that the air does not include particles of formulation which have been intentionally added but is not intended to imply that the normal surrounding air has been filtered or treated to remove all particles although filtering can take place. Air is the preferred gas to use with drug delivery, it being noted that other non-toxic gases, e.g., $CO_2$ can be used.

The terms "particles", "aerosolized particles" and "aerosolized particles of formulation" are used interchangeably herein and shall mean particles of formulation comprised of the protonated/acidified nucleic acids of the invention. Any of these is preferable with a carrier, (e.g., a pharmaceutically active respiratory drug and carrier). The particles have a size that is sufficiently small such that when the particles are formed they remain suspended in the air for a sufficient amount of time such that the patient can inhale the particles into the patient's lungs. The particles have a size in the range of 0.1 μm to about 50 μm, preferably 0.5 to 10 μm. Particle diameter is an aerodynamic diameter.

The term "substantially dry" shall mean protonated/acidified nucleic acid in a container or in particles of an aerosol that contain less than 10% free water, ethanol or other liquid carrier based on total weight and preferably contains no detectable free liquid carrier.

The term "dosage unit" shall mean the administration of nucleic acids to a patient in need thereof by the intrapulmonary route of administration which may encompass one or more releases of formulation from a dispensing device (from one or more containers) over a period of time of 15 minutes or less, preferably 10 minutes or less, and more preferably 5 minutes or less, during which period one or more inhalations are made by the patient and one or more doses of nucleic acid are released and inhaled.

The terms "nucleic acid" and "nucleic acid molecule", as used interchangeably herein, refer to a molecule comprised of nucleotides, i.e., ribonucleotides, deoxyribonucleotides, or both. The term includes monomers and polymers of ribonucleotides and deoxyribonucleotides, with the ribonucleotides and/or deoxyribonucleotides being connected together, in the case of the polymers, via 5' to 3' linkages. However, linkages may include any of the linkages known in the nucleic acid synthesis art including, for example, nucleic acids comprising 5' to 2' linkages. The nucleotides used in the nucleic acid molecule may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, and the like.

The term "oligonucleotide" as used herein refers to a nucleic acid molecule comprising from about 2 to about 100 nucleotides, more preferably from 2 to 80 nucleotides, and even more preferably from about 4 to about 35 nucleotides.

The term "monomer" as used herein refers to a nucleic acid molecule and derivatives thereof comprised of a single nucleotide.

The terms "modified oligonucleotide", "modified monomer", and "modified nucleic acid molecule" as used herein refer to nucleic acids with one or more chemical modifications at the molecular level of the natural molecular structures of all or any of the nucleic acid bases, sugar moieties, internucleoside phosphate linkages, as well as molecules having added substituents, such as diamines, cholesteryl or other lipophilic groups, or a combination of modifications at these sites. The internucleoside phosphate linkages can be phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate and/or sulfone internucleotide linkages, or 3'-3', 2'-5', or 5'-5' linkages, and combinations of such similar linkages (to produce mixed backbone modified oligonucleotides). The modifications can be internal (single or repeated) or at the end(s) of the oligonucleotide molecule and can include additions to the molecule of the internucleoside phosphate linkages, such as cholesteryl, diamine compounds with varying numbers of carbon residues between amino groups and terminal ribose, deoxyribose and phosphate modifications which cleave or cross-link to the opposite chains or to associated enzymes or other proteins. Electrophilic groups such as ribose-dialdehyde could covalently link with an epsilon amino group of the lysyl-residue of such a protein. A nucleophilic group such as n-ethylmaleimide tethered to an oligomer could covalently attach to the 5' end of an mRNA or to another electrophilic site. The term modified oligonucleotides also includes oligonucleotides comprising modifications to the sugar moieties such as 2'-substituted ribonucleotides, or deoxyribonucleotide monomers, any of which are connected together via 5' to 3' linkages. Modified oligonucleotides may also be comprised of PNA or morpholino modified backbones where target specificity of the sequence is maintained.

The term "nucleic acid backbone" as used herein refers to the structure of the chemical moiety linking nucleotides in a molecule. This may include structures formed from any and all means of chemically linking nucleotides. A modified backbone as used herein includes modifications to the chemical linkage between nucleotides, as well as other modifications that may be used to enhance stability and affinity, such as modifications to the sugar structure. For example an α-anomer of deoxyribose may be used, where the base is inverted with respect to the natural β-anomer. In a preferred embodiment, the 2'-OH of the sugar group may be altered to 2'-O-alkyl or 2'-O-alkyl-n(O-alkyl), which provides resistance to degradation without comprising affinity.

The terms "acidification" and "protonation/acidification" as used interchangeably herein refer to the process by which protons (or positive hydrogen ions) are added to proton acceptor sites on a nucleic acid. The proton acceptor sites include the amine groups on the base structures of the nucleic acid and the phosphate of the phosphodiester linkages. As the pH is decreased, the number of these acceptor sites which are protonated increases, resulting in a more highly protonated/acidified nucleic acid.

The term "protonated/acidified nucleic acid" refers to a nucleic acid that, when dissolved in water at a concentration of approximately 16 $A_{260}$ per ml, has a pH lower than physiological pH, i.e., lower than approximately pH 7. Modified nucleic acids, nuclease-resistant nucleic acids, and antisense nucleic acids are meant to be encompassed by this definition. Generally, nucleic acids are protonated/acidified by adding protons to the reactive sites on a nucleic acid, although other modifications that will decrease the pH of the nucleic acid can also be used and are intended to be encompassed by this term.

The term "end-blocked" as used herein refers to a nucleic acid with a chemical modification at the molecular level that prevents the degradation of selected nucleotides, e.g., by nuclease action. This chemical modification is positioned such that it protects the integral portion of the nucleic acid, for example the coding region of an antisense oligonucleotide. An end block may be a 3' end block or a 5' end block. For example, a 3' end block may be at the 3'-most position of the molecule, or it may be internal to the 3' ends, provided it is 3' to the integral sequences of the nucleic acid.

The term "substantially nuclease resistant" refers to nucleic acids that are resistant to nuclease degradation, as compared to naturally occurring or unmodified nucleic acids. Modified nucleic acids of the invention are at least 1.25 times more resistant to nuclease degradation than their unmodified counterpart, more preferably at least 2 times more resistant, even more preferably at least 5 times more resistant, and most preferably at least 10 times more resistant than their unmodified counterpart. Such substantially nuclease resistant nucleic acids include, but are not limited to, nucleic acids with modified backbones such as phosphorothioates, methylphosphonates, ethylphosphotriesters, 2'-O-methylphosphorothioates, 2'-O-methyl-p-ethoxy ribonucleotides, 2'-O-alkyls, 2'-O-alkyl-n (O-alkyl)s, 2'-fluoros, 2'-deoxy-erythropentofuranosyls, 2'-O-methyl ribonucleosides, methyl carbamates, methyl carbonates, inverted bases (e.g., inverted T's), or chimeric versions of these backbones.

The term "substantially acid resistant" as used herein refers to nucleic acids that are resistant to acid degradation as compared to unmodified nucleic acids. Typically, the relative acid resistance of a nucleic acid will be measured by comparing the percent degradation of a resistant nucleic acid with the percent degradation of its unmodified counterpart (i.e., a corresponding nucleic acid with "normal" backbone, bases, and phosphodiester linkages). A nucleic acid that is acid resistant is preferably at least 1.5 times more resistant to acid degradation, or at least 2 times more resistant, even more preferably at least 5 times more resistant, and most preferably at least 10 times more resistant than their unmodified counterpart.

The term "alkyl" as used herein refers to a branched or unbranched saturated hydrocarbon chain containing 1–6 carbon atoms, such as methyl, ethyl, propyl, tert-butyl, n-hexyl and the like.

The term "gene involved in a pulmonary disorder" as used herein refers to any gene which by its expression is involved in the infection, progression, or virulence of a disease or disorder. For example, a gene involved in a pulmonary disorder may be any gene involved in replication of the fungal organism *Pneumocystis carinii*. Suppression of expression of such a gene would interfere with the replication and thus the progression of the pneumonia caused by this organism. In another example, a gene involved in a pulmonary disorder may be a gene defective in a patient which is causative of a genetic disorder, e.g., CF. The expression of an introduced exogenous human form of the CFR gene (the gene defective in CF patients) may alleviate the symptoms of the disease by providing a functional form of the CFR protein. In yet another example, a gene involved in a pulmonary disorder may be an endogenous human gene that is overexpressed in the patient, e.g., an oncogene involved in small cell carcinoma. Suppression of expression of the oncogene using an antisense oligonucleotide targeted to the oncogene may halt progression and/or metastasis of the disease.

The terms "treatment", "treating" and the like as used herein generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in an animal, particularly a human, and includes:

(a) preventing a respiratory disease from occurring in a subject that may be predisposed to the disease but has not yet been diagnosed as having it;

(b) inhibiting a respiratory disease, i.e., arresting its development; or (c) relieving a respiratory disease, i.e., causing regression and/or amelioration of the disease. The invention is particularly directed toward treating patients with any infectious bacteria.

GENERAL ASPECTS OF THE INVENTION

This invention is based on the discovery that protonated/acidified nucleic acids of any sequence and any length represent a new class of antibiotics effective against both drug-resistant and antibiotic susceptible bacteria in vitro and in vivo. Specifically, protonated/acidified nucleic acids of the invention are effective antibacterial agents against all bacterial species, and can be used to treat or prevent bacterial infection in people and animals. Thus, the present invention includes protonated, nuclease resistant nucleic acids and methods of producing them to be effective at killing bacteria or inhibiting bacterial growth. In particular, the present invention specifically relates to the process of protonation to facilitate the antibacterial action of nucleic acids against pathogenic bacteria.

In addition, nucleic acids presently used therapeutically for the treatment of other diseases or disorders, e.g., antisense nucleic acids targeted to a specific gene, can also be protonated/acidified, thereby conferring the additional therapeutic effect of anti-bacterial activity on such nucleic acids. Thus, the present invention also includes the use of nucleic acids to treat or prevent diseases involving viral infection, cancer, fungal infections, etc., that are additionally protonated in order to simultaneously treat or prevent a bacterial infection.

Protonation/acidification can be utilized to confer on a nucleic acid the ability to function as an antibacterial agent. Acidification of nucleic acids is the process by which protons (or positive hydrogen ions) are added to the reactive sites on a nucleic acid. As the number of reactive sites that are protonated increases, the pH is decreased, and the bacterial inhibiting activity of the nucleic acid is increased. Accordingly, the nucleic acids of the invention are protonated/acidified to give a pH when dissolved in water of less than pH 7 to about pH 1, or in preferred embodiments, pH 6 to about 1 or pH 5 to about 1. In other preferred embodiments, the dissolved nucleic acids have a pH from pH 4.5 to about 1 or, in a preferred embodiment, a pH of 4.0 to about 1, or, in a more preferred embodiment, a pH of 3.0 to about 1, or, in another more preferred embodiment, a pH of 2.0 to about 1.

In a preferred embodiment, the protonated/acidified nucleic acids of the compositions and methods of the invention are substantially nuclease resistant, substantially acid resistant, and preferably, both substantially nuclease resistant and substantially acid resistant. This embodiment includes nucleic acids completely derivatized by phosphorothioate linkages, 2'-O-methyl-phosphodiesters, 2'-O-alkyls, 2'-O-alkyl-n(O-alkyl)s, 2'-fluoros, 2'-deoxy-erythropentofuranosyls, p-isopropyl nucleic acids, phosporamidates, chimeric linkages, and any other backbone modifications. This embodiment also includes other modifications that render the nucleic acids substantially resistant to endogenous nuclease activity. Methods of rendering a nucleic acid nuclease resistant include, but are not limited to, covalently modifying the purine or pyrimidine bases that comprise the nucleic acid. For example, bases may be methylated, hydroxymethylated, or otherwise substituted (e.g., glycosylated) such that the nucleic acids comprising the modified bases are rendered substantially nuclease resistant.

In the most preferred embodiment the protonated/acidified nucleic acid will have a backbone substantially resistant to acid degradation, exonuclease digestion, and endonuclease digestion.

Typically, the relative nuclease resistance of a nucleic acid can be measured by comparing the percent digestion of a resistant nucleic acid with the percent digestion of its unmodified counterpart (i.e., a corresponding nucleic acid with "normal" backbone, bases, and phosphodiester linkage). Percent degradation may be determined by using analytical HPLC to assess the loss of full length nucleic acids, or by any other suitable methods (e.g., by visualizing the products on a sequencing gel using staining, autoradiography, fluorescence, etc., or measuring a shift in optical density). Degradation is generally measured as a function of time.

Comparison between unmodified and modified nuleic acids can be made by ratioing the percentage of intact modified nucleic acid to the percentage of intact unmodified nucleic acid. For example, if, after 15 minutes of exposure to a nuclease, 25% (i.e., 75% degraded) of an unmodified nucleic acid is intact, and 50% (i.e., 50% degraded) of a modified nucleic acid is intact, the modified nucleic acid is said to be 2 times (50% divided by 25%) more resistant to nuclease degradation than is the unmodified nucleic acid. Generally, a substantially nuclease resistant nucleic acid will be at least about 1.25 times more resistant to nuclease degradation than an unmodified nucleic acid with a corresponding sequence, typically at least about 1.5 times more resistant, preferably about 1.75 times more resistant, and more preferably at least about 10 times more resistant after 15 minutes of nuclease exposure.

Percent acid degradation may be determined by using analytical HPLC to assess the loss of full length nucleic acids, or by any other suitable methods (e.g., by visualizing the products on a sequencing gel using staining, autoradiography, fluorescence, etc., or measuring a shift in optical density). Degradation is generally measured as a function of time.

Comparison between unmodified and modified nucleic acids can be made by ratioing the percentage of intact modified nucleic acid to the percentage of intact unmodified nucleic acid. For example, if, after 30 minutes of exposure to a low pH environment, 25% (i.e., 75% degraded) of an unmodified nucleic acid is intact, and 50% (i.e., 50% degraded) of a modified nucleic acid is intact, the modified nucleic acid is said to be 2 times (50% divided by 25%) more resistant to nuclease degradation than is the unmodified nucleic acid. Generally, substantially "acid resistant" nucleic acids will be at least about 1.25 times more resistant to acid degradation than an unmodified nucleic acid with a corresponding sequence, typically at least about 1.5 times more resistant, preferably about 1.75 more resistant, and more preferably at least about 10 times more resistant after 30 minutes of exposure at 37° C. to a pH of about 1.5 to about 4.5.

The presently described purified nucleic acids may be used as the sole therapeutic agent, or they may be complexed with additional antibacterial or other therapeutic agents. For example, the described nuclease-resistant antibacterial nucleic acids may be linked to a conventional antibiotic or other chemical group that inhibits bacterial gene expression. Alternatively, the purified nucleic acids may be included in a therapeutic composition with agents designed for the alleviation of other disorders and/or symptoms, e.g., decongestants, antihistamines, anti-nausea agents, sedatives, pain relievers and the like. In another example, the nucleic acids may be an antisense molecule directed to the suppression of a gene involved in inflammation, e.g phosphodiesterase-4. Additionally, the antibacterial nucleic acid may be complexed with a variety of well established compounds or structures that, for instance, further enhance the in vivo stability of the nucleic acid, or otherwise enhance its pharmacological properties (e.g., increase in vivo half-life, reduce toxicity, promote bioavailability, etc.).

The sequence of the nucleic acids of the invention may vary, as the antibacterial effect of the modified nucleic acids is not dependent on the sequence. For example, nucleic acids directed at treating a bacterial infection may be complementary to a known bacterial gene that is needed for bacterial growth. In another example, the nucleic acid of the invention may have no substantial sequence homology with any sequence in the genome of the bacterium that causes the infection being treated or prevented. In yet another example, nucleic acids directed at other therapeutic targets, e.g., viruses, cancer cells, fungal infections, may also be protonated/acidified according to the invention to function simultaneously as antibacterial agents in addition to their primary therapeutic function. In this manner, therapeutics designed to suppress an immune response or to suppress oncogenesis, metastasis, dedifferentiation, or angiogenesis can simultaneously treat or prevent a secondary bacterial infection, which can be associated with the primary indication. Antisense sequences used for the treatment of disorders such as inflammation, cancer, viral infections, fungal infections, and the like can be determined by one skilled in the art upon reading this disclosure.

Bactericidal and/or bacteristatic activity of the nucleic acids of the invention may be measured using any number of methods available to those skilled in the art. One example of such a method is measurement of antibacterial activity through use of a MIC (minimal inhibitory concentration) test that is recognized to be predictive of in vivo efficacy for the treatment of a bacterial infection with antibiotics. The nucleic acids of the invention display antibacterial activity in this test, even without pretreatment of the bacteria to permeabilize the membrane and without PEG-modification of the nucleic acids.

Protonation/acidification of nucleic acids with a range of chemical alterations may be used in the invention, although a preferred embodiment of the present invention is a protonated/acidified nucleic acid with the chemical structure of 5'-butanol-2'-O-alkyl RNA-butanol-3' or 2'-O-alkyl-O-alkyl, that has a pH of 3 to 1 when dissolved in water. A particularly preferred embodiment of the present invention is a protonated/acidified nucleic acid with the chemical backbone structure of 5'-butanol-2'-O-methyl RNA-butanol-3', that has a pH of 3 to 1 when dissolved in water.

Nucleic Acid Synthesis

Nucleic acids can be synthesized on commercially purchased DNA synthesizers from <1 uM to >1 mM scales using standard phosphoramidite chemistry and methods that are well known in the art, such as, for example, those disclosed in Stec et al., 1984, *J Am. Chem. Soc.* 106:6077–6089, Stec et al., 1985, *J Org. Chem.* 50(20):3908–3913, Stec et al., 1985, *J Chromatog.* 326:263–280, LaPlanche et al., 1986, *Nuc. Acid. Res.* 14(22):9081–9093, and Fasman, 1989, *Practical Handbook of Biochemistry and Molecular Biology*, 1989, CRC Press, Boca Raton, Fla., herein incorporated by reference.

Nucleic acids can be purified by any method known to those in the art. In a preferred embodiment, they are purified by chromatography on commercially available reverse phase or ion exchange media, e.g., Waters Protein Pak, Pharmacia's Source Q, etc. Peak fractions can be combined and the samples desalted and concentrated by means of reverse phase chromatography on a poly(styrene-divinylbenzene) based media, e.g., Hamilton's PRP1 or PRP3, or Polymer Labs' PLRP resins. Alternatively, ethanol precipitation, diafiltration, or gel filtration may be used followed by lyophilization or solvent evaporation under vacuum in commercially available instrumentation such as Savant's Speed Vac. Optionally, small amounts of the nucleic acids may be electrophoretically purified using polyacrylamide gels.

Lyophilized or dried-down preparations of nucleic acids can be dissolved in pyrogen-free, sterile, physiological saline (i.e., 0.85% saline), sterile Sigma water, and filtered through a 0.45 micron Gelman filter (or a sterile 0.2 micron pyrogen-free filter). The described nucleic acids may be partially or fully substituted with any of a broad variety of chemical groups or linkages including, but not limited to: phosphoramidates; phosphorothioates; alkyl phosphonates; 2'-O-methyl; 2'-modified RNA; morpholino groups; phosphate esters; propyne groups; or chimerics of any combination of the above groups or other linkages (or analogues thereof).

A variety of standard methods can be used to purify the presently described antibacterial nucleic acids. In brief, the antibacterial nucleic acids of the present invention can be purified by chromatography on commercially available reverse phase media (for example, see the RAININ Instrument Co., Inc. instruction manual for the DYNAMAX®-300A, Pure-DNA reverse phase columns, 1989, or current updates thereof, herein incorporated by reference) or ion exchange media such as Waters' Protein Pak or Pharmacia's Source Q (see generally, Warren and Vella, 1994, "Analysis and Purification of Synthetic Nucleic Acids by High-Performance Liquid Chromatography", in *Methods in Molecular Biology*, vol. 26; *Protocols for Nucleic acid Conjugates*, S. Agrawal, ed. Humana Press, Inc., Totowa, N.J.; Aharon et al., 1993, *J Chrom.* 698:293–301; and Millipore Technical Bulletin, 1992, *Antisense DNA: Synthesis, Purification, andAnalysis*). Peak fractions can be combined and the samples concentrated and desalted via alcohol (ethanol, butanol, isopropanol, and isomers and mixtures thereof, etc.) precipitation, reverse phase chromatography, diafiltration, or gel filtration.

A nucleic acid is considered pure when it has been isolated so as to be substantially free of, inter alia, incomplete nucleic acid products produced during the synthesis of the desired nucleic acid. Preferably, a purified nucleic acid will also be substantially free of contaminants which may hinder or otherwise mask the antibacterial activity of the oligonucleotide. A purified nucleic acid, after acidification by one of the disclosed methods or by any other method known to those of skill in the art, is a protonated/acidified nucleic acid that has been isolated so as to be substantially free of, inter alia, excess protonating/acidifying agent. In general, where a nucleic acid is able to bind to, or gain entry into, a target cell to modulate a physiological activity of interest, it shall be deemed as substantially free of contaminants that would render the nucleic acid less useful.

In particular embodiments, the nucleic acids of the invention are composed of one or more of the following: partially or fully substituted phosphorothioates; phosphonates; phosphate esters; phosphoroamidates; 2'-modified RNAs; 3'-modified RNAs; peptide nucleic acids; propynes or analogues thereof The nucleic acids may be completely or partially derivatized by a chemical moeity including, but not limited to, phosphodiester linkages, phosphotriester linkages, phosphoramidate linkages, siloxane linkages, carbonate linkages, carboxymethylester linkages, acetamidate linkages, carbamate linkages, thioether linkages, bridged phosphoramidate linkages, bridged methylene phosphonate linkages, phosphorothioate linkages, methylphosphonate linkages, phosphorodithioate linkages, morpholino, bridged phosphorothioate linkages, sulfone internucleotide linkages, 3'-3' linkages, 5'-2' linkages, 5'-5'linkages, 2'-deoxy-erythropentofuranosyl, 2'-fluoro, 2'-O-alkyl nucleotides, 2'-O-alkyl-n(O-alkyl) phosphodiesters, morpholino linkages, p-ethoxy oligonucleotides, PNA linkages, p-isopropyl oligonucleotides, or phosphoramidates.

Protonated/Acidified Nucleic Acids

Subsequent to, or during, the above synthesis and purification steps, protonated/acidified forms of the described nucleic acids can be generated by subjecting the purified, or partially purified, or crude nucleic acids, to a low pH, or acidic, environment. Purified or crude nucleic acids can be protonated/acidified with acid, including, but not limited to, phosphoric acid, nitric acid, hydrochloric acid, acetic acid, etc. For example, acid may be combined with nucleic acids in solution, or alternatively, the nucleic acids may be dissolved in an acidic solution. Excess acid may be removed by chromatography or in some cases by drying the nucleic acid.

Other procedures to prepare protonated nucleic acids known to the skilled artisan are equally contemplated to be within the scope of the invention. Once the nucleic acids of the present invention have been protonated they may be separated from any undesired components like, for example, excess acid. The skilled artisan would know of many ways to separate the oligonucleotides from undesired components. For example, the oligonucleotide solution may be subjected to chromatography following protonation. In a preferred embodiment, the oligonucleotide solution is run over a poly(styrene-divinyl benzene) based resin (e.g., Hamilton's PRP-1 or 3 and Polymer Lab's PLRP) following protonation.

The protonated/acidified nucleic acids can be used directly, or in a preferred embodiment, processed further to remove any excess acid and salt via precipitation, reverse phase chromatography, diafiltration, or gel filtration. The protonated/acidified oligos can be concentrated by precipitation, lyophilization, solvent evaporation, etc. When suspended in water or saline, the acidified nucleic acid preparations of the invention typically exhibit a pH of between 1 and 4.5 depending upon the level of protonation/acidification, which can be determined by how much acid is used in the acidification process. Alternatively, nucleic acids can be protonated by passage over a cation exchange column charged with hydrogen ions.

Acid and Nuclease Resistant Nucleic Acids

Generally, nucleic acid preparations near pH 2 to 1 demonstrate better antibacterial activity than nucleic acids at or near pH 4.5. Many oligo backbones are not stable at pH 2 and experience depurination, although a number of backbones are relatively stable at a pH of 4 to 5. It has been discovered that 2'-O-alkyl, 3'-O-alkyl, and 2'-O-alkyl-n(O-alkyl) nucleic acids are stable at the desired pH of 2 to 1.

In one embodiment, the invention uses nucleic acids that are substantially nuclease resistant. This includes nucleic acids completely derivatized by phosphorothioate linkages, 2'-O-methylphosphodiesters, 2'-O-alkyl, 2'-O-alkyl-n(O-alkyl), 2'-fluoro, 2'-deoxy-erythropentofuranosyl, p-ethoxy, morpholino nucleic acids, p-isopropyl nucleic acids, phosphoramidates, chimeric linkages, and any other backbone modifications, as well as other modifications, which render the nucleic acids substantially resistant to endogenous nuclease activity. Additional methods of rendering nucleic acids nuclease resistant include, but are not limited to, covalently modifying the purine or pyrimidine bases that comprise the nucleic acid. For example, bases may be methylated, hydroxymethylated, or otherwise substituted (e.g., glycosylated) such that the nucleic acids comprising the modified bases are rendered substantially nuclease resistant.

Although 2'-O-alkyl substituted nucleic acids and molecules with similar modifications exhibit marked acid stability and endonuclease resistance, they are sensitive to 3' exonucleases. In order to enhance the exonuclease resistance of 2'-O-alkyl substituted nucleic acids, the 5' and 3' ends of the ribonucleic acid sequence are preferably attached to an exonuclease blocking function. For example, one or more phosphorothioate nucleotides can be placed at either end of the oligoribonucleotide. Additionally, one or more inverted bases can be placed on either end of the oligoribonucleotide, or one or more alkyl, e.g., butanol-substituted nucleotides or chemical groups can be placed on one or more ends of the oligoribonucleotide. An enzyme-resistant butanol preferably has the structure $CH_2CH_2CH_2CH_2$—OH (4-hydroxybutyl) which is also referred to as a C4 spacer. Accordingly, a preferred embodiment of the present invention is a protonated/acidified nucleic acid comprising an antibacterial nucleic acid having the following structure:

A-B-C wherein "B" is a 2'-O-alkyl or 2'-O-alkyl-n(O-alkyl) oligoribonucleotide between about 1 and about 98 bases in length, and "A" and "C" are respective 5' and 3' end blocking groups (e.g., one or more phosphorothioate nucleotides (but typically fewer than six), inverted base linkages, or alkyl, alkenyl, or alkynl groups or substituted nucleotides). A partial list of blocking groups includes inverted bases, dideoxynucleotides, methylphosphates, alkyl groups, aryl groups, cordycepin, cytosine arabanoside, 2'-methoxyethoxy nucleotides, phosphoramidates, a peptide linkage, dinitrophenyl group, 2'- or 3'-O-methyl bases with phosphorothioate linkages, 3'-O-methyl bases, fluorescein, cholesterol, biotin, acridine, rhodamine, psoralen, and glyceryl.

Therapeutic Use of Antibacterial Nucleic Acids

When used in the therapeutic treatment of disease, an appropriate dosage of an antibacterial protonated/acidified nucleic acid, or mixture thereof, may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Additionally, therapeutic dosages may also be altered depending upon factors such as the severity of infection, and the size or species of the host. Additionally, pulmonary infections may be treated both parenterally and by direct application of suitably formulated forms of the antibacterial nucleic acids to the lung by inhalation therapy.

Given that bacterial infection is a particularly problematic secondary complication in immuno-compromised individuals, such as patients suffering from acquired immuno-deficiency disease syndrome (AIDS), HIV infected individuals, patients undergoing chemotherapy or radiation therapy, etc., an additional embodiment of the presently described invention is the use of a therapeutic nucleic acid that has a viral, cancer, fungal or other target, wherein the nucleic acid is additionally protonated/acidified so it can also serve as an antibacterial nucleic acid. The gene may be targeted against a vital gene of a foreign organism, e.g., a yeast replication gene or a viral structural protein. This allows simultaneous treatment of a primary infection by one class of organism and prevention or treatment of a secondary bacterial infection. For example, a protonated/acidified antisense gene targeted to *Pneumocystis carinii* in an AIDS patient will both target the fungal infection, but will also treat or prevent a simultaneous or subsequent opportunistic bacterial infection. The nucleic acid will address its primary target by affecting the expression or activity of the gene of interest, but in addition it will function as an antibacterial agent.

Alternatively, the nucleic acid may be directed against expression of an endogenous gene in the pulmonary cells, for example using a lipid carrier-nucleic acid mixture. See U.S. Pat. No. 5,641,662, which describes transfection of lung cells via aerosolized transgene delivery and is incorporated herein by reference. This may be extremely useful for gene therapy treatment of genetic disorders such as cystic fibrosis, in which a functioning exogenous human CFR gene may be introduced. This may also be useful for cancers such as small cell lung carcinoma, in which enhanced or suppressed expression of an endogenous gene or expression of an exogenous gene may be effective. See U.S. Pat No. 5,849,863, which is incorporated herein by reference. Other potential therapeutic uses involving both endogenous and exogenous human genes can also be used, as will be apparent to those skilled in the art.

In another embodiment, the protonated/acidified nucleic acid is administered in conjunction with a separate therapeutic agent. For example, the nucleic acid of the invention may be administered with an agent that reduces the viscosity of mucus in a patient ailing from a pulmonary disorder involving thickened or accumulated mucous secretions. See e.g. U.S. Pat. No. 5,698,537, which describes the pulmonary delivery of phospholipids for this purpose. In another example, the nucleic acid of the invention may be administered with an anti-inflammatory agent, which will be effective for treatment of bacterial infections in subjects. Examples of bacterial organisms against which the methods of the invention are effective include gram positive bacteria, gram negative bacteria, acid fast bacteria, mycobacteria, *Staphylococcus aureus, Streptococcus pyogenes, Streptococcus pneumoniae* and *Escherichia coli*. The methods of the invention are effective against infection by all bacterial organisms, including members of the following genera: Aerococcus, Listeria, Streptomyces, Chlamydia, Actinomadura, Lactobacillus, Eubacterium, Arachnia, Mycobacterium, Peptostreptococcus, Staphylococcus, Corynebacterium Erysipelothrix, Dermatophilus, Rhodococcus, Ribodobacterium, Pseudomonas, Streptococcus, Bacillus, Peptococcus, Pneumococcus, Micrococcus, Neisseria, Klebsiella, Kurthia, Nocardia, Nocardiopsis, Serratia, Rothia, Escherichia, Propionibacterium, Actinomyces, Helicobacter, Enterococcus, Shigella, Vibrio, Clostridia, Salmonella, Yersinia, and Haemophilus.

Pharmaceutical Compositions and Delivery

Formulations for dry powder devices may either comprise bare nucleic acid structures, nucleic acids in viral or mammalian vectors, or vesicles structures. The presently described protonated/acidified antibacterial nucleic acids are preferably formulated with a variety of physiological carrier molecules. These molecules can function to stabilize the nucleic acid composition, enhance the dispersion of the particles, and/or facilitate delivery of the nucleic acids to a particular cell type or location.

The dose of nucleic acid administered can be controlled by varying a number of physical properties of the composition and the dosage unit to best deliver the compositions to the desired site in the lungs in the desired dose. For example, with certain pulmonary delivery devices more composition should be used per dosage unit if a patient has a low inspiratory rate, whereas less is needed for a patient with a high inspiratory rate. The dosage unit may be delivered in a single dose, or a dosage unit may be repeatedly delivered to a patient at the same measured inspiratory flow rate (in the range of 0.1 to 2.0 liters/second) and separately determined inspiratory volume (in the range of 0.15 to 1.5 liters).

Delivery of particles can also be controlled, in part, by adjusting particle sizes. The particle size should be large enough that it is deposited in the lungs and not expelled upon exhale, but small enough that the nucleic acids are available with an adequate surface area for proper absorption into the target cells.

In addition to adjusting particle size, delivery of the protonated/acidified nucleic acids can be obtained by releasing an aerosolized dose at a desired point in a patient's respiratory cycle. For example, to achieve deposition of particles in the lower respiratory tract, e.g., to treat pneumonia, it is desirable to get the aerosolized formulation deeply into the lung.

The presently described antibacterial nucleic acids may also be complexed with molecules that enhance their ability to enter the target cells. Examples of such molecules include, but are not limited to, carbohydrates, polyamines, amino acids, peptides, lipids, and molecules vital to bacterial growth. For example, the antibacterial nucleic acids may be combined with a lipid, cationic lipid, or anionic lipid (which may be preferred for protonated/acidified nucleic acids). The resulting nucleic acid/lipid emulsion, or liposomal suspension may, inter alia, effectively increase the in vivo half-life of the nucleic acid. Examples of suitable anionic lipids for use with protonated/acidified nucleic acids include, but are not limited to, cardiolipin, dimyristoyl, dipalmitoyl, or dioleoyl phosphatidyl choline or phosphatidyl glycerol, palmitoyloleoyl phosphatidyl choline or phosphatidyl glycerol, phosphatidic acid, lysophosphatidic acid, phosphatidyl serine, phosphatidyl inositol, and anionic forms of cholesterol. The use of cationic, anionic, and/or neutral lipid compositions or liposomes is generally described in International Publications Nos. WO90/14074, WO 91/16024, WO 91/17424, and U.S. Pat. No. 4,897,355, herein incorporated by reference. By assembling the antibacterial nucleic acids into lipid-associated structures, the protonated/acidified antibacterial nucleic acids may be targeted to specific bacterial cell types by the incorporation of suitable targeting agents (i.e., specific antibodies or receptors) into the nucleic acid/lipid complex.

The protonated/acidified nucleic acid will be formulated in pharmaceutically acceptable compositions suitable for pulmonary or respiratory delivery to a mammalian host, usually a human host at risk of or suffering from osteoporosis. Particular formulations include dry powders, liquid solutions or suspensions suitable for nebulization, and propellant formulations suitable for use in metered dose inhalers (MDI's). The preparation of such formulations is well described in the patent, scientific, and medical literatures, and the following descriptions are intended to be exemplary only.

Dry powder formulations will typically comprise the protonated/acidified nucleic acid in a dry, usually lyophilized, form with a particle size within a preferred range for deposition within the alveolar region of the lung, typically from 0.5 $\mu$m to 5 $\mu$m. Respirable powders of protonated/acidified nucleic acid within the preferred size range can be produced by a variety of conventional techniques, such as jet-milling, spray-drying, solvent precipitation, and the like. Dry powders can then be administered to the patient in conventional dry powder inhalers (DPI's) that use the patient's inspiratory breath through the device to disperse the powder or in air-assisted devices that use an external power source to disperse the powder into an aerosol cloud.

Formulations for dry powder can include hydrophilic excipient material. Preferably, such excipients function to enhance dispersion of the nucleic acid in dry powder aerosols, enhance wetting of the nucleic acid constructs as they are delivered in the body, and stabilize the nucleic acid constructs. See WO 96/32116, published Oct. 17, 1996 and incorporated herein by reference.

Dry powder devices typically require a powder mass in the range from about 1 mg to 10 mg to produce a single aerosolized dose ("puff"). Since the required dose of protonated/acidified nucleic acid will generally be much lower than this amount, as discussed below, the protonated/acidified nucleic acid powder will typically be combined with a pharmaceutically acceptable dry bulking powder, with the protonated/acidified nucleic acid present usually at from about 1% to 10% by weight. Preferred dry bulking powders include sucrose, lactose, trehalose, human serum albumin (HSA), and glycine. Other suitable dry bulking powders include cellobiose, dextrans, maltotriose, pectin, sodium citrate, sodium ascorbate, mannitol, and the like.

Typically, suitable buffers and salts may be used to stabilize the protonated/acidified nucleic acid in solution prior to particle formation. Suitable buffers include phosphate, citrate, acetate, and tris-HCl, typically at concentrations from about 5 mM to 50 mM. Suitable salts include sodium chloride, sodium carbonate, calcium chloride, and the like. Other additives, such as chelating agents, peptidase inhibitors, and the like, which would facilitate the biological activity of the protonated/acidified nucleic acid once it is dissolved within the lung would be appropriate. For example, ethylenediaminetetraacetic acid (EDTA) would be useful as a chelator for divalent cations that are peptidase cofactors.

Liquid formulations of protonated/acidified nucleic acid for use in nebulizer systems can employ slightly acidic buffers (pH 4–6) with protonated/acidified nucleic acid concentrations of from about 1 mg/ml to 20 mg/ml. Suitable buffers include acetate, ascorbate, and citrate, at concentrations of 5 mM to 50 mM. These buffers can act as antioxidants, or other physiologically acceptable antioxidants can be added to protect free methionines in the protonated/acidified nucleic acid against oxidation. Other components may be added to enhance or maintain chemical stability, including chelating agents, protease inhibitors, isotonic modifiers, inert gases, and the like.

For use in MDI's, the protonated/acidified nucleic acid of the present invention will be dissolved or suspended in a suitable aerosol propellant, such as a chlorofluorocarbon (CFC) or a hydrofluorocarbon (HFC). Suitable CFC's include trichloromonofluoromethane (propellant 11), dichlorotetrafluoromethane (propellant 114), and dichlorodifluoromethane (propellant 12). Suitable HFC's include tetrafluoroethane (HFC-134a) and heptafluoropropane (HFC-227).

Preferably, for incorporation into the aerosol propellant, the protonated/acidified nucleic acid of the present invention will be processed into respirable particles as described for the dry powder formulations. The particles are then suspended in the propellant, typically being coated with a surfactant to enhance their dispersion. Suitable surfactants include oleic acid, sorbitan trioleate, and various long chain diglycerides and phospholipids.

Such aerosol propellant formulations may further include a lower alcohol, such as ethanol (up to 30% by weight) and other additives to maintain or enhance chemical stability and physiological acceptability. Pulmonary or respiratory administration of protonated/acidified nucleic acid according to the present invention will be especially useful in the treatment of cystic fibrosis or asthma, where the protonated/acidified nucleic acid can be administered in combination with anti-inflammatory therapeutics. Such treatment methods are well described in U.S. Pat. Nos. 4,698,328 and 4,833,125, the disclosures of which have previously been incorporated herein by reference.

The total aerosolized dosage of protonated/acidified nucleic acid for the treatment of bacterial infection will typically be in range from about 100 $\mu$g to 2,000 $\mu$g per day, usually being in the range from about 250 $\mu$g to 1000 $\mu$g per day. Such dosages will result in a total systemic availability (i.e., amount that is delivered to the blood) in the range from about 50 $\mu$g to 500 $\mu$g per day, usually from 100 $\mu$g to 250 $\mu$g, per day. Precise dosages will, of course, vary depending on the activity of the particular protonated/acidified nucleic acid or analogue employed, and other known pharmacokinetic factors. Usually, the total dosage of protonated/acidified nucleic acid will be delivered in a plurality of separate aerosolized doses, typically being at least two, and often being from three to ten, where each aerosolized bolus contains from 50 $\mu$g to 500 $\mu$g of the protonated/acidified nucleic acid.

Pulmonary delivery of protonated/acidified nucleic acids according to the methods of the present invention has been found to provide a desired pulsatile serum concentration profile. The pulsatile serum protonated/acidified nucleic acid concentration profile will typically peak within 30 minutes after administration, with serum concentrations falling rapidly, typically to below 50% of maximum within 30 minutes of the peak and to below 25% within 60 minutes of the peak.

Formulations for dry powder devices may either comprise bare nucleic acid structures, nucleic acids in viral or mammalian vectors, or vesicles structures. In the case of a dry powder formulation, a sufficient amount of dry bulking powder will be added so that a total dosage of protonated/acidified nucleic acids within the above range can be achieved with one or more aerosolized boluses which are to be inhaled by the patient. Typically, the active protonated/acidified nucleic acid will be present at from about 1% to 25% by weight of the powder, with aerosolized boluses including from 1 mg to 10 mg of the powder. Liquid formulations suitable for use in nebulizers typically have a concentration of the protonated/acidified nucleic acids in the range from about 1 mg/ml to 20 mg/ml, with the total volume of nebulized liquid needed to deliver the bolus in the range from about 0.1 ml to 1 ml. The aerosol propellant formulations will be delivered by MDI at about 0.5 mg to 5 mg of protonated/acidified nucleic acids per aerosol dose. Because of the inefficiencies of MDI devices, only a small portion, typically in the range of 5% to 20%, of the drug will reach the lungs. Thus, a sufficient amount of the protonated/acidified nucleic acids can be delivered in from two to five aerosolized boluses, with about 0.1 to 1 mg of the protonated/acidified nucleic acid in each of the boluses.

Aerosols can be prepared by dissolving or suspending the nucleic acid in a propellant such as ethyl alcohol or in propellant and solvent phases. The pharmaceutical compositions for topical or aerosol form will generally contain from about 0.01% by weight (of the nucleic acid) to about 40% by weight, preferably about 0.02% to about 10% by weight, and more preferably about 0.05% to about 5% by weight depending on the particular form employed.

There are several different types of devices that use generally different mechanisms and methodologies to produce aerosols for inhalation. The most commonly used device is a metered dose inhaler (MDI) which comprises a drug formulation container with the formulation including a low boiling point propellant. The formulation is held in the container under pressure and a metered dose of formulation is released as an aerosol when the valve on the container is opened. The low boiling point propellant quickly evaporates or "flashes" when the formulation is exposed to atmospheric pressure outside the container. The particles of formulation containing the drug without the propellant are inhaled into the patient's lungs and thereafter migrate into the patient's circulatory system. There are a number of different types of MDI devices. Devices of this type are described in U.S. Pat. Nos. 5,404,871 and 5,364,838.

Another type of aerosol delivery device forces a formulation through a porous membrane. Formulation moving through the pores breaks up to form small particles which are inhaled by the patient. Devices of this type are shown in U.S. Pat. Nos. 5,554,646 and 5,522,385.

Yet another type of device is the dry powder inhaler (DPI) device. As indicated by the name such devices use formulations of dry powder in which powder is blown into an aerosolized cloud via a burst of gas. Typical DPI devices are shown in U.S. Pat. Nos. 5,458,135, 5,492,112, 5,622,166, and 5,775,320.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1
Bacterial Growth Studies
Limited Nutrient Growth Study

For the limited nutrient growth study, cells were taken off plates and suspended in PBS to give a final concentration of $10^5$ CFU/ml and a final volume of 1 ml. Mueller-Hinton broth was added (40 µl for *S. aureus* ACC #13301, 20 µl for *P. aeruginosa* ACC #10145). 100 µl of water or 100 µl of nucleic acid (32 $A_{260}$ units, 2'-O-methyl ribonucleotides, phosphodiester linkage, 5' and 3' inverted T end-blocked, sequence CGCCATTGG, SEQ ID NO: 1) was added, and the tubes were incubated at 35° C. without shaking for approximately 24 hours. The $A_{625}$ was measured and the percent inhibition calculated as a percent of the control. The results are in the following table:

| Bacteria | pH of Nucleic Acid | Inhibition of Growth (%) |
|---|---|---|
| S. aureus | Water Control-pH 7 | 0 |
| S. aureus | 2 | 100 |
| S. aureus | 3 | 100 |
| S. aureus | 4 | 100 |
| S. aureus | 5 | 16 |
| S. aureus | 7 | 0 |
| P. aeruginosa | Water Control-pH 7 | 0 |
| P. aeruginosa | 2 | 100 |
| P. aeruginosa | 3 | 100 |
| P. aeruginosa | 4 | 100 |
| P. aeruginosa | 5 | 0 |
| P. aeruginosa | 7 | 0 |

Stationary Growth Study

A stationary growth assay was also performed to study the effect of pH on the anti-bacterial activity of nucleic acids. Cells were taken off plates and suspended in saline to give a final concentration of $10^7$ CFU/ml of *S. aureus* in 1 ml of PBS. 100 µl of water or 100 µl of nucleic acid (32 $A_{260}$ units, 2'-O-methyl ribonucleotides, phosphodiester linkage, 5' and 3' inverted T end blocked, sequence CGCCATTGG, SEQ ID NO: 1) was added, and the tubes were incubated at 35° C. without shaking for approximately 24 hours. Aliquots were plated directly or after dilutions and incubated at 37° C. and colonies counted after 24 hours. The results are in the following table:

| Bacteria | pH of Nucleic Acid | CFU/ml |
|---|---|---|
| S. aureus | Water Control-pH 7 | $10^7$ |
| S. aureus | 2 | 0 |
| S. aureus | 3 | $10^3$ |
| S. aureus | 4 | $10^6$ |
| S. aureus | 5 | $10^7$ |
| S. aureus | 7 | $10^7$ |

From these results, it was concluded that lowering the pH of a nucleotide conferred upon it bactericidal and bacteriostatic effects. Next, the effect of sequence identity and length were explored.

Example 2
Sequence Effects on Antibacterial Activity
Stationary Growth Study First, a stationary growth assay was performed to study the effect of sequence length. Cells were taken off plates and suspended in saline to give a final concentration of $10^7$ CFU/ml of *Strep. mutans* in 1 ml of PBS. 50 µl of water or 50 µl of nucleic acids of varying length (16 $A_{260}$ units) were added and the tubes incubated at 35° C. without shaking for approximately 24 hours. Each of the nucleic acids used consisted of 2'-O-methyl substituted ribonucleotides phosphodiester linked with 5' and 3' inverted T end-blocking. The sequences were: 114.6-CGCCAT (SEQ ID NO: 2); 114.12-ACGCGCCATTGG (SEQ ID NO: 3); 114.21-GGAACGCGCCATTGGTATATC (SEQ ID NO: 4). The lengths reported in the following table for each nucleic acid include the inverted T's at the 5' and 3' ends. Aliquots were plated directly or after dilutions and incubated at 37° C. and colonies counted after 24 hours. The results are in the following table:

| Bacteria | Nucleic Acid | Length (Bases) | pH | Inhibition (%) | CFU/ml |
|---|---|---|---|---|---|
| Strep. mutans | Water Control | 0 | 7 | 0 | $10^7$ |
| Strep. mutans | 114.6 | 8 | 3 | 100 | 0 |
| Strep. mutans | 114.12 | 14 | 3 | 100 | 0 |
| Strep. mutans | 114.21 | 23 | 3 | 100 | 0 |
| Strep. mutans | 114.6 | 8 | 7 | 0 | $10^7$ |
| Strep. mutans | 114.12 | 14 | 7 | 0 | $10^7$ |
| Strep. mutans | 114.21 | 23 | 7 | 0 | $10^7$ |

Limited Nutrient Growth Study

Next, a limited nutrient growth assay was performed to study the effects of nucleotide homopolymers (AAAAAAAAAAAA, SEQ ID NO: 5; UUUUUUUUUUUU, SEQ ID NO: 6; GGGGGGGGGGGG, SEQ ID NO: 7; CCCCCCCCCCCC, SEQ ID NO: 8). Each homopolymer used consisted of 2'-O-methyl substituted ribonucleotides phosphodiester linked, with both 3' and 5' butanol end-blocking. Cells were taken off plates and suspended to give a final concentration of $10^5$ CFU/ml in 1 ml of PBS. Mueller-Hinton broth was added (40 µl for *S. aureus* ACC #13301, 20 µL for *P. aeruginosa* ACC #10145). 100 µl of water or 100 µl of nucleic acid at pH 1.5 (32 $A_{260}$ units) were added and the tubes were incubated at 350° C. without shaking for approximately 24 hours. The $A_{625}$ was measured and the percent inhibition calculated as a percent of the control. The results are in the following table:

| Bacteria | Oligonucleotide, pH 1.5 | Inhibition (%) |
|---|---|---|
| S. aureus | Water Control - pH 7 | 0 |
| S. aureus | Homopolymer, 12 A | 100 |
| S. aureus | Homopolymer, 12 C | 100 |
| S. aureus | Homopolymer, 12 G | 100 |
| S. aureus | Homopolymer, 12 U | 100 |
| P. aeruginosa | Water Control - pH 7 | 0 |
| P. aeruginosa | Homopolymer, 12 A | 100 |
| P. aeruginosa | Homopolymer, 12 C | 100 |
| P. aeruginosa | Homopolymer, 12 G | 100 |
| P. aeruginosa | Homopolymer, 12 U | 100 |

Next, a limited nutrient growth assay was performed to study the effects of monomers, dimers and trimers. Each nucleic acid used consisted of 2'-O-methyl substituted ribonucleotides phosphodiester linked, with both 3' and 5' blocking with butanol. The nucleic acid designated 114.12 had a sequence of ACGCGCCATTAT, SEQ ID NO: 9. Cells were taken off plates and suspended to give a final concentration of $10^5$ CFU/ml in 1 ml of PBS. Mueller-Hinton broth was added (40 µl for *S. aureus* ACC #13301, 20 µl for *E. Coli*

ACC #35218). 25 µl of water or 25 µl of nucleic acid at pH 1.5 (8 $A_{260}$ units) were added and the tubes were incubated at 35° C. without shaking for approximately 24 hours. The $A_{625}$ was measured and the percent inhibition calculated as a percent of the control. Aliquots were plated directly or after dilutions and incubated at 37° C. and colonies counted after 24 hours to determine CFUs. The results are in the following table:

| Bacteria | Nucleic Acid | Length (Bases) | Inhibition (%) | CFU/ml |
|---|---|---|---|---|
| S. aureus | Water Control | 0 | 0 | $10^6$ |
| S. aureus | G | 1 | 100 | $10^3$ |
| S. aureus | U | 1 | 100 | $10^2$ |
| S. aureus | GU | 2 | 100 | $10^3$ |
| S. aureus | AUG | 3 | 100 | $10^3$ |
| S. aureus | 114.12 | 12 | 100 | $10^3$ |
| E. coli | Water Control | 0 | 0 | $10^8$ |
| E. coli | G | 1 | 100 | $10^3$ |
| E. coli | U | 1 | 100 | $10^2$ |
| E. coli | GU | 2 | 100 | $10^3$ |
| E. coli | AUG | 3 | 100 | $10^4$ |
| E. coli | 114.12 | 12 | 100 | $10^3$ |

A stationary phase assay was performed to study the effects of monomers, dimers and trimers. Each nucleic acid used consisted of 2'-O-methyl substituted ribonucleotides phosphodiester linked, with both 3' and 5' blocking with butanol. The nucleic acid designated 114.12 had a sequence of ACGCGCCATTAT, SEQ ID NO: 9. Cells were taken off plates and suspended in saline to give an $A_{625}$ of 0.08 for S. aureus, 0.12 for E. coli, and 0.1 for K. pneumoniae in 1 ml of PBS. 25 µl of water or 25 µl of nucleic acid (8 $A_{260}$ units) were added and the tubes incubated at 35° C. without shaking for approximately 24 hours. Aliquots were plated directly or after dilutions and incubated at 37° C. and colonies counted after 24 hours to determine CFUs. The results are in the following table:

| Bacteria | Nucleic Acid | Length (Bases) | CFU/ml |
|---|---|---|---|
| S. aureus | Water Control | 0 | $10^6$ |
| S. aureus | G | 1 | 0 |
| S. aureus | U | 1 | 0 |
| S. aureus | GU | 2 | 0 |
| S. aureus | AUG | 3 | 0 |
| S. aureus | 114.12 | 12 | 0 |
| E. coli | Water Control | 0 | $10^7$ |
| E. coli | G | 1 | 0 |
| E. coli | U | 1 | 0 |
| E. coli | GU | 2 | 0 |
| E. coli | AUG | 3 | 0 |
| E. coli | 114.12 | 12 | 0 |
| K. pneumoniae | Water Control | 0 | $10^8$ |
| K. pneumoniae | G | 1 | $10^2$ |
| K. pneumoniae | U | 1 | $10^1$ |
| K. pneumoniae | GU | 2 | $10^1$ |
| K. pneumoniae | AUG | 3 | $10^1$ |
| K. pneumoniae | 114.12 | 12 | $10^2$ |

In conclusion, these results demonstrate that the ability of protonated/acidified nucleic acids to function as an antibacterial agent is independent of sequence identity. Furthermore, homopolymers and nucleic acids as short as monomers are also effective. These results indicate that although sequence may play a role in the activity of the oligonucleotide, there is also another mechanism of the anti-bacterial effect which is not antisense dependent, and is thus sequence independent.

Example 3
Efficacy in Topical Treatment of Ear Infections

Protonated/acidified nucleic acids were very effective in treating outer ear epidermal infections in chinchillas caused by *Pseudomonas aeruginosa* bacteria. All the chinchilla infected ears that received continued protonated/acidified nucleic acid treatment were completely cured four days after treatment began.

Chinchillas' ears were infected with *Pseudomonas aeruginosa* bacteria. Specifically, the maceration of the epidermal layer of the chinchillas' ears was caused by prolonged exposure of the ears to water. This helps create a receptive environment for the Pseudomonas infection in the epidermal layer of skin lining in the chinchillas' ear canals. Cotton plegets were saturated with a suspension of washed *Pseudomonas aeruginosa* and were inserted in the ear canals of the chinchillas. The plegets were removed after 48 hours.

Treatment of the chinchillas began on day 3 post infection, when the ears were judged to have a "level 3" severity as determined by otoscopic examination. The chinchillas received two daily topical applications of either 400 µl of protonated/acidified nucleic acids at pH 1.5 of sequence ACGCGCCATTAT, SEQ ID NO: 9, in water (2.8 nMolar) or 400 µl of the protonated/acidified nucleic acids of identical sequence (2 µmMolar) in a vehicle mixture (water/ethanol/propylene glycol). The nucleic acid consisted of 2'-O-methyl substituted ribonucleotides, phosphodiester linked and end blocked with butanol at both the 5' and 3' ends. The chinchillas were examined daily to assess the effectiveness of treatment based on the degree of severity of the ear infections.

The results of the protonated/acidified nucleic acid treatment indicated that all of the treated chinchillas' ears showed a significant reduction in the severity of ear infections, as determined by otoscopic examination. Significant improvements could be observed after 3 treatments of protonated/acidified nucleic acids. The chinchillas received treatment for an additional 4 to 5 days. Untreated control chinchillas showed no improvement over this time frame. In contrast, all ear infections that received continued protonated/acidified nucleic acids treatment were completely cured by day 7 post infection (i.e., 4 days after treatment began with protonated/acidified nucleic acids).

In addition, there were slight differences in the progression of healing between protonated/acidified nucleic acids dissolved in the two transport mediums, water or the vehicle mixture (water/ethanol/propylene glycol). Based on otoscopic examination, protonated/acidified nucleic acids in the vehicle mixture were slightly more effective in treating the ear infections.

In conclusion, protonated/acidified nucleic acids have demonstrated effectiveness in treating chinchillas' outer ear infections caused by *Pseudomonas aeruginosa*. This is significant since this infectious bacteria is naturally an antibiotic-resistant bacteria.

Example 4
Pulmonary Delivery of Protonated/Acidified Monomers

The acidified/protonated monomers are tested for efficacy in pulmonary delivery by examining the ability of the modified nucleic acids to inhibit growth of *P. aeruginosa* using a rodent model system. In the described embodiment, the modified monomer is encapsulated in a liposome prior to pulmonary delivery.

Microencapsulation

Liposomes containing protonated/acidified nucleic acids are prepared using the dehydration-rehydration method of Legace et al. (*J Microencapsulation*, 8:53–61(1991). The liposomes are constructed using a 10:1 ratio of DPPC, a non-charged phospholipid, and DMPG, a negatively charged lipid. An appropriate amount of lipid mixture is dissolved in chloroform in a round bottom flask and dried to a lipid film by rotoevaporation (Bucci Rotavapor-KRvr 65/45) at 65° C. under vacuum conditions. The lipids are then redissolved 1:20 in phosphate buffered saline, lyophilized, and rehydrated in a mixture of 3mM protonated/acidified guanine monomer (pH 4.5) dissolved in sterile, deionized water. The encapsulated monomer is both protonated and end blocked with butanol at both the 5' and 3' ends.

Infection and Treatment

An isolate of *P. aeruginosa* ACC #10145 is cultured for 18 hours shaking in Proteose Peptone broth (Difco Laboratories, Detroit, Mich.). Chronic *P. aeruginosa* respiratory infection is induced in 40 adult Sprague-Dawley rats, weighing approximately 200 g each, which are equally divided into an experimental group and a control group. The *P. aeruginosa*, is introduced to the rats as described in Omri et al., *Antimicrob. Agents Chemother.* 38:1090–1095 (1994), which involves an intratracheal administration of the culture to anesthetized rats. A suspension containing approximately $5 \times 10^5$ CFU/100 µl *P. aeruginosa* is administered intratracheally to each anesthetized animal.

Three days after inoculation, the animals are treated with doses of the liposome encapsulated modified cytosine monomer. Twenty rats in the experimental group receive three doses at 16 hour intervals of 0.1 ml of the liposome encapsulated oligonucleotide. The oligonucleotide is administered at a total concentration of approximately 100 mg of protonated monomer. Twenty rats in the control group are treated with an equivalent amount of liposome-entrapped water.

Sixteen hours after the last treatment, the rats are anesthetized and exsanguinated. The lungs are removed and homogenized in cold sterile PBS (40% [wt/vol]) for 30 seconds. The lung homogenate is then diluted serially in PBS and plated and cultured in duplicate onto Proteose Peptone no. 2 agar plates (Difco Laboratories). After an overnight incubation the number of CFU for each dilution is determined.

Animals with protonated/acidified monomer treatment exhibit effective bactericidal activity against *P. aeruginosa*. The number of colonies observed are significantly reduced, showing about a 50% growth inhibition in comparison to the control animals.

Example 5

Pulmonary Delivery of Ptotonated/Acidified Oligonucleotides

The acidified/protonated oligonucleotides are also tested for efficacy in pulmonary delivery using a rodent model system and a commercially available jet nebulizer. The oligonucleotide used in these experiments is protonated/acidified ACGCGCCATTAT, SEQ ID NO: 9, dissolved in sterile water (2.8 mMolar). The nucleic acid consists of 2'-O-methyl substituted deoxyribonucleotides, phosphodiester linked and end blocked with butanol at both the 5' and 3' ends. The oligonucleotides may either be microencapsulated for pulmonary delivery, or may be administered directly as naked nucleic acid.

Microencapsulation

Liposomes containing protonated/acidified oligonucleotides are prepared using the remote-loading procedure of Oh et al., *Antimicrob. Agents Chemother.*, 39:2104–2111 (1995), which utilizes an ammonium sulfate gradient.

Infection and Treatment

Broth cultures of modified Mueller-Hinton broth (Difco Laboratories) are inoculated with an *F. tularensis* live vaccine strain #296684 (ATCC, Rockville, Md.) and incubated at 37° C. for 4 to 5 days. 80 six-week-old Balb/c female mice are anesthetized and each infected intranasally with a dosage equal to the $LD_{50}$ of the *F. tularensis* culture, which is generally about 50 µl per mouse.

At 24 hours post-infection, the mice are placed in a 24-port nose-only aerosol exposure chamber. The first experimental group of 20 mice are exposed to aerosolized liposome-encapsulated modified oligonucleotide, generated using the PurRD Raindrop nebulizer (Puritan-Bennett, Lenoxa, Kansas). The second experimental group of 20 mice are exposed to aerosolized naked modified oligonucleotide dissolved in water, also aerosolized using the PurRD Raindrop nebulizer. The first control group receive aerosolized liposome-encapsulated water, and the second control group receive an aerosolized volume of water. The infected animals are monitored daily for signs of symptoms and for death from the infection. At 14 days post-infection, the number of mice surviving the infection is determined.

Both the mice receiving the liposome-encapsulated oligonucleotide and the mice receiving the naked oligonucleotide exhibited a 55–60% survival rate, whereas both control groups had a 0% survival rate.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of treating a pulmonary bacterial infection in a mammalian subject, said method comprising the steps of:

aerosolizing a formulation to create particles comprising a nucleic acid comprising a backbone structure modified from that of a naturally occurring nucleotide polymer the nucleic acid being protonated to an extent that the nucleic acid exhibits a pH in a range of about 0 to about 5 at a concentration of 1 mg/ml of water and the nucleic acid is characterized by a pH stability of at least one hour at pH about 1 to about 5; and inhaling the aerosolized formulation into lungs of a patient and allowing aerosolized particles of the formulation to deposit on lung tissue.

2. The method of claim 1, wherein the aerosolized particles of formulation have a diameter in a range from about 1 micron to about 5 microns.

3. The method of claim 1, wherein the nucleic acid comprises: a substitution at a residue on a ribose group and a blocking chemical modification at the 3' terminus of the nucleic acid.

4. The method of claim 3, wherein the formulation is in a solid form and wherein the formulation has a pH of about 0 to less than 5 when dissolved at 1 mg/ml in water.

5. The method of claim 3, wherein the nucleic acid comprises 3'-5' internucleoside linkages, and wherein a 2' residue on a ribose group is substituted, said substitution distinguishing the nucleic acid from a naturally occurring nucleotide RNA or DNA.

6. The method of claim 3, wherein the nucleic acid comprises 2'-5' internucleoside linkages, and wherein the 3' residue on a ribose group is substituted, said substitution distinguishing the nucleic acid from a naturally occurring nucleotide RNA or DNA.

7. The method of claim 1, wherein the nucleic acid is comprised of about 2 to about 100 nucleotides.

8. The method of claim 1, wherein the nucleic acid is selected from the group consisting of partially substituted phosphorothioate, fully substituted phosphorothioate, phosphonate, phosphate ester, phosphoramidate, 2'-modified RNA, 3'-modified DNA, peptide nucleic acid, propyne, and combinations thereof.

9. The method of claim 1, wherein the nucleic acid is completely or partially derivatized by a chemical moiety selected from the group consisting of phosphodiester linkages, phosphotriester linkages, phosphoramidate linkages, siloxane linkages, carbonate linkages, carboxymethylester linkages, acetamidate linkages, carbamate linkages, thioether linkages, bridged phosphoramidate linkages, bridged methylene phosphonate linkages, phosphorothioate linkages, methylphosphonate linkages, phosphorodithioate linkages, bridged phosphorothioate linkages, sulfone internucleotide linkages, 3'-3' linkages, 2'-5' linkages, 5'-5' linkages, 2'-deoxy-erythropentofuranosyl, 2'-fluoro, 2'-O-alkyl nucleotides, 2'-O-alkyl-n(O-alkyl) phosphodiesters, morpholino linkages, p-ethoxy oligonucleotides, PNA linkages, and p-isopropyl oligonucleotides.

10. The method of claim 1, wherein the formulation comprises a monomer having a structure modified from that of a naturally occurring nucleotide monomer; and one or more exogenous protons introduced to reactive sites on said monomer, wherein the nucleic acid is characterized by a pH stability of at least one hour in pH of 0.01 to 5, and wherein the nucleic acid exhibits substantial antibacterial activity.

11. The method of claim 10, further comprising a blocking chemical modification at the 5' position of the monomer and a blocking chemical modification at the 3' position of the monomer.

12. The method of claim 10, wherein the nucleic acid has a pH of from 0.5 to 5.

13. The method of claim 10, wherein the nucleic acid further comprises a substitution at the 2' position of the ribose group relative to a naturally occurring ribonucleotide or deoxyribonucleotide.

14. The method of claim 1, wherein the pulmonary infection is a *Psuedomonas aeruginosa* infection.

15. The method of claim 1, wherein the pulmonary infection is a *Staphylococcus aureus* infection.

* * * * *